(12) United States Patent
Flores et al.

(10) Patent No.: US 12,714,581 B2
(45) Date of Patent: Aug. 25, 2026

(54) ADDITIVE MANUFACTURING TECHNIQUES FOR PROTECTIVE DEVICES

(71) Applicant: Hanger, Inc., Austin, TX (US)

(72) Inventors: Aaron Flores, Austin, TX (US); Antonio Dias, Scottsdale, AZ (US); Justin Mieth, Austin, TX (US)

(73) Assignee: Hanger, Inc., Austin, TX (US)

( * ) Notice: Subject to any disclaimer, the term of this patent is extended or adjusted under 35 U.S.C. 154(b) by 268 days.

(21) Appl. No.: 17/547,507

(22) Filed: Dec. 10, 2021

(65) Prior Publication Data

US 2022/0183861 A1 Jun. 16, 2022

Related U.S. Application Data

(60) Provisional application No. 63/124,230, filed on Dec. 11, 2020.

(51) Int. Cl.
*A61F 2/58* (2006.01)
*A61F 2/50* (2006.01)
(Continued)

(52) U.S. Cl.
CPC ............. *A61F 2/58* (2013.01); *A61F 2/5046* (2013.01); *A61F 2/78* (2013.01); *A61F 2/80* (2013.01);
(Continued)

(58) Field of Classification Search
CPC ...... A61F 2002/5052; A61F 2002/5053; A61F 2/5046; A61F 2/58; A61F 2/78;
(Continued)

(56) References Cited

U.S. PATENT DOCUMENTS

| | | | |
|---|---|---|---|
| 667,534 | A | 2/1901 | Kimball |
| 2,790,254 | A | 4/1957 | Burns |

(Continued)

FOREIGN PATENT DOCUMENTS

| | | |
|---|---|---|
| BR | 112018004850 | 8/2023 |
| CA | 2664803 | 4/2008 |

(Continued)

OTHER PUBLICATIONS

Rogers, B., Advanced trans-tibial socket fabrication using selective laser sintering, Prosthetics and Orthotics International, Mar. 2007, No. 31, pp. 88-100.

(Continued)

*Primary Examiner* — Bruce E Snow
(74) *Attorney, Agent, or Firm* — Foley & Lardner LLP

(57) ABSTRACT

A protective device for an upper extremity post-operative residual limb of a user. The protective device includes a multi-section shell having a shape that corresponds to an anatomical structure of the upper extremity post-operative residual limb of the user. The protective device also includes a hinge coupled with a first section and a second section of the multi-section shell, the hinge configured to facilitate relative rotation of the first section and the second section to transition the protective device between an open configuration and a closed configuration. The multi-section shell is configured to receive one or more attachments to increase functionality of the upper extremity post-operative residual limb of the user.

20 Claims, 5 Drawing Sheets

(51) Int. Cl.
*A61F 2/78* (2006.01)
*A61F 2/80* (2006.01)
*B33Y 50/00* (2015.01)
*B33Y 80/00* (2015.01)
*G05B 19/4099* (2006.01)

(52) U.S. Cl.
CPC ............... *B33Y 50/00* (2014.12); *B33Y 80/00* (2014.12); *G05B 19/4099* (2013.01); *A61F 2002/5049* (2013.01); *A61F 2002/505* (2013.01); *A61F 2002/7862* (2013.01)

(58) Field of Classification Search
CPC ................ A61F 2002/7862; A61F 2/54; A61F 2002/543; A61F 2002/546; A61F 2/583; A61F 2/588; A61F 2/7812; A61F 2/80
See application file for complete search history.

(56) References Cited

U.S. PATENT DOCUMENTS 3,490,078 A * 1/1970 Perez, Jr. ................ A61F 2/588 279/100
4,134,159 A 1/1979 Wilson
4,283,800 A 8/1981 Wilson
4,702,255 A 10/1987 Schenkl
5,458,657 A 10/1995 Rasmusson
5,653,766 A * 8/1997 Naser ........................ A61F 2/80 623/32
6,428,494 B1 8/2002 Schwenn et al.
6,605,118 B2 8/2003 Capper et al.
6,669,736 B2 12/2003 Slemker et al.
7,162,075 B2 1/2007 Littlefield et al.
7,227,979 B2 6/2007 Littlefield et al.
7,242,798 B2 7/2007 Littlefield et al.
7,356,379 B2 4/2008 Slemker et al.
8,838,263 B2 9/2014 Sivak et al.
9,161,848 B2 10/2015 Tompkins
9,232,827 B1 1/2016 Penn
9,402,760 B2 8/2016 Gordon et al.
9,469,075 B2 10/2016 Zachariasen et al.
9,480,581 B2 11/2016 Layman et al.
9,486,334 B2 11/2016 Tompkins
9,610,731 B2 4/2017 Zachariasen
9,738,036 B2 8/2017 Littlefield
9,873,229 B2 1/2018 Chun et al.
9,908,295 B2 3/2018 Ou et al.
9,987,801 B2 6/2018 Littlefield
10,010,433 B2 7/2018 Layman et al.
10,089,662 B2 10/2018 Norman
10,241,498 B1 3/2019 Beard et al.
10,357,383 B2 7/2019 Tompkins
10,463,525 B2 11/2019 Littlefield et al.
10,517,746 B2 12/2019 Bernhardt et al.
10,528,032 B2 1/2020 Schouwenburg et al.
10,561,521 B2 2/2020 Littlefield et al.
10,603,203 B2 3/2020 Littlefield et al.
10,624,767 B2 4/2020 Jonsson et al.
10,639,173 B2 5/2020 Walter
10,682,846 B2 6/2020 Littlefield et al.
10,695,211 B2 6/2020 Mottram et al.
10,703,084 B2 7/2020 Littlefield et al.
10,710,356 B2 7/2020 Littlefield et al.
10,726,617 B2 7/2020 Littlefield et al.
10,766,246 B2 9/2020 Nauka et al.
10,846,925 B2 11/2020 Littlefield et al.
10,905,568 B2 2/2021 Erenstone
11,086,148 B2 8/2021 Chumbley et al.
D943,753 S 2/2022 Grygar
2004/0068337 A1 4/2004 Watson et al.
2004/0260402 A1 12/2004 Baldini et al.
2005/0038522 A1 2/2005 Helenberger et al.
2006/0094951 A1 5/2006 Dean et al.
2007/0055383 A1 3/2007 King
2007/0081717 A1 4/2007 Littlefield
2007/0213839 A1 9/2007 Nachbar
2007/0225824 A1 9/2007 Einarsson
2007/0265727 A1 11/2007 Bae et al.
2009/0132056 A1 5/2009 Kania
2013/0046394 A1 2/2013 Lipschutz et al.
2013/0274896 A1 10/2013 Wang et al.
2014/0379097 A1 12/2014 Hurley et al.
2015/0018974 A1* 1/2015 Dillingham ............... A61F 2/76 623/32
2015/0142150 A1 5/2015 Layman et al.
2015/0250715 A1 9/2015 Adams et al.
2015/0265434 A1 9/2015 Hurley et al.
2016/0074182 A1 3/2016 Celebi et al.
2016/0287425 A1 10/2016 Gilmer et al.
2017/0318900 A1 11/2017 Charlesworth et al.
2018/0281312 A1 10/2018 Littlefield et al.
2018/0353308 A1 12/2018 Tompkins
2019/0015238 A1 1/2019 Mottram et al.
2020/0188141 A1 6/2020 Muller
2021/0024775 A1 1/2021 Rolland et al.
2021/0137708 A1 5/2021 Orrason et al.
2021/0275326 A1* 9/2021 Dechev ..................... A61F 2/68
2021/0322200 A1 10/2021 Goodnough
2021/0338459 A1* 11/2021 Tompkins ................. A61F 2/80
2021/0401596 A1* 12/2021 Hunter .................... A61F 2/586
2022/0175571 A1 6/2022 Goodnough
2022/0183861 A1* 6/2022 Flores ................... A61F 2/5046
2022/0211522 A1 7/2022 Polta et al.
2023/0149201 A1 5/2023 Smith et al.

FOREIGN PATENT DOCUMENTS

CA 3171895 9/2019
CN 102209965 10/2011
CN 106537410 3/2017
CZ 2022189 11/2023
DE 10 2010 019 843 A1 11/2011
DE 10 2018 133 486 A1 6/2020
EP 2 735 290 A1 5/2014
EP 3 815 650 A1 5/2021
GB 2103490 A * 2/1983 ............... A61F 2/80
JP 2023-094208 7/2023
KR 101675400 11/2016
KR 20180127120 11/2018
WO WO-94/04102 A1 3/1994
WO WO-98/40038 A1 9/1998
WO WO-2013/142343 A1 9/2013
WO WO-2014/113581 7/2014
WO WO-2014/130878 A1 8/2014
WO WO-2015/073793 A1 5/2015
WO WO-2017/042550 A1 3/2017
WO WO-2017/151577 A1 9/2017
WO WO-2018/115874 A1 6/2018
WO WO-2019/178686 A1 9/2019
WO WO-2020/069817 A1 4/2020
WO WO-2022/091453 5/2022

OTHER PUBLICATIONS

Davies, S., "HP 3D printing tech & nTopology Design software enables prosthetic device manufacture in Guatemala." Oct. 13, 2021, 3D Printing and Additive Manufacturing Intelligence.
Fairley, Miki. "3D Printing Gains Momentum in Clinical O&P." The O&P EDGE Magazine, Jan. 3, 2022, opedge.com/3d-printing-gains-momentum-in-clinical-op/.
International Search Report and Written Opinion for International Application No. PCT/US2017/015981, mail date May 11, 2017, 14 pages.
International Search Report and Written Opinion issued on PCT/US2023/032048 dated Mar. 13, 2024.
International Search Report and Written Opinion on PCT/US2023/036863 dated Mar. 15, 2024.
Extended European Search Report issued on EP23863740.9 dated Nov. 12, 2025.

* cited by examiner

ADDITIVE MANUFACTURING TECHNIQUES FOR PROTECTIVE DEVICES

CROSS-REFERENCE TO RELATED PATENT APPLICATION

This application claims the benefit of and priority to U.S. Provisional Application No. 63/124,230, filed Dec. 11, 2020, the entire disclosure of which is incorporated by reference herein.

BACKGROUND

The present disclosure relates generally to prosthetics and orthotics. More particularly, the present disclosure relates to additive manufacturing or protective devices, prosthetics and/or orthotics.

SUMMARY

One implementation of the present disclosure is a protective device for an upper extremity post-operative residual limb of a user, according to some embodiments. In some embodiments, the protective device includes a multi-section shell having a shape that corresponds to an anatomical structure of the upper extremity post-operative residual limb of the user. In some embodiments, the protective device also includes a hinge coupled with a first section and a second section of the multi-section shell, the hinge configured to facilitate relative rotation of the first section and the second section to transition the protective device between an open configuration and a closed configuration. In some embodiments, the multi-section shell is configured to receive one or more attachments to increase functionality of the upper extremity post-operative residual limb of the user.

In some embodiments, the protective device is configured for use with a patient's partial hand. In some embodiments, the multi-section shell is configured to fully enclose around the patient's partial hand.

In some embodiments, the one or more attachments are implemented in a design process of the protective device to supplement the patient's ability to interact with surroundings. In some embodiments, the multi-section shell is configured to undergo deformation without sustaining structural damage.

In some embodiments, the protective device further includes one or more fitted straps configured to couple with strap mounting portions, the straps configured to fasten with themselves. In some embodiments, the multi-section shell is configured to fit contours and structures of the upper extremity post-operative residual limb of the user. In some embodiments, the multi-section shell includes a foam layer that is positioned on an interior of the multi-section shell. In some embodiments, the foam layer is configured to directly abut the upper extremity post-operative residual limb of the user.

Another embodiment of the present disclosure is a method for manufacturing a protective device for an upper extremity post-operative residual limb of a patient, according to some embodiments. In some embodiments, the method includes using a digital scanner to capture either an anatomical structure of the patient's upper extremity post-operative residual limb or an anatomical structure of a cast of the patient's upper extremity post-operative residual limb to generate a scan file. In some embodiments, the method includes converting the scan file to a design file, modifying the design file, and additively manufacturing the design file to produce the protective device using an additive manufacturing device.

In some embodiments, modifying the design file includes using build-ups or reductions to a thickness of a shell of the design file. In some embodiments, the protective device has a variable thickness along a dimension of the upper extremity prosthetic socket. In some embodiments, the variable thickness is configured to accommodate the anatomy of the upper extremity post-operative residual limb of the patient. In some embodiments, the method includes providing a protective dressing or gauze onto the upper extremity post-operative residual limb of the patient prior to using the digital scanner to capture the anatomical structure of the patient's upper extremity post-operative residual limb.

In some embodiments, the design file is at least one of a computer assisted design (CAD) file or a computer assisted manufacturing (CAM) file. In some embodiments, the additive manufacturing device is a 3d printer configured to provide layers of material on top of each other in succession to produce the protective device.

In some embodiments, the method further includes uploading the design file to the additive manufacturing device. In some embodiments, the protective device includes the shell, a hinge, and strap mounting hardware.

In some embodiments, the method further includes installing one or more straps to the strap mounting hardware. In some embodiments, the shell, the hinge, and the strap mounting hardware are produced by the additive manufacturing device using a uniform material composition. In some embodiments, the shell is a multi-section shell configured to transition between an open position and a closed position.

Another implementation of the present disclosure is a protective device for an upper extremity post-operative residual limb of a user manufactured using additive manufacturing, according to some embodiments. In some embodiments, the protective device includes a multi-section shell having a shape that corresponds to an anatomical structure of the upper extremity post-operative residual limb of the user. In some embodiments, the protective device also includes a hinge coupled with a first section and a second section of the multi-section shell, the hinge configured to facilitate relative rotation of the first section and the second section to transition the protective device between an open configuration and a closed configuration. In some embodiments, the multi-section shell has a thickness that varies spatially along the multi-section shell, the thickness at a particular location being based on a corresponding amount of expected stress to be experienced by the multi-section shell at the particular location during use of the protective device.

In some embodiments, the multi-section shell is configured to receive one or more attachments to increase functionality of the upper extremity post-operative residual limb of the user.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
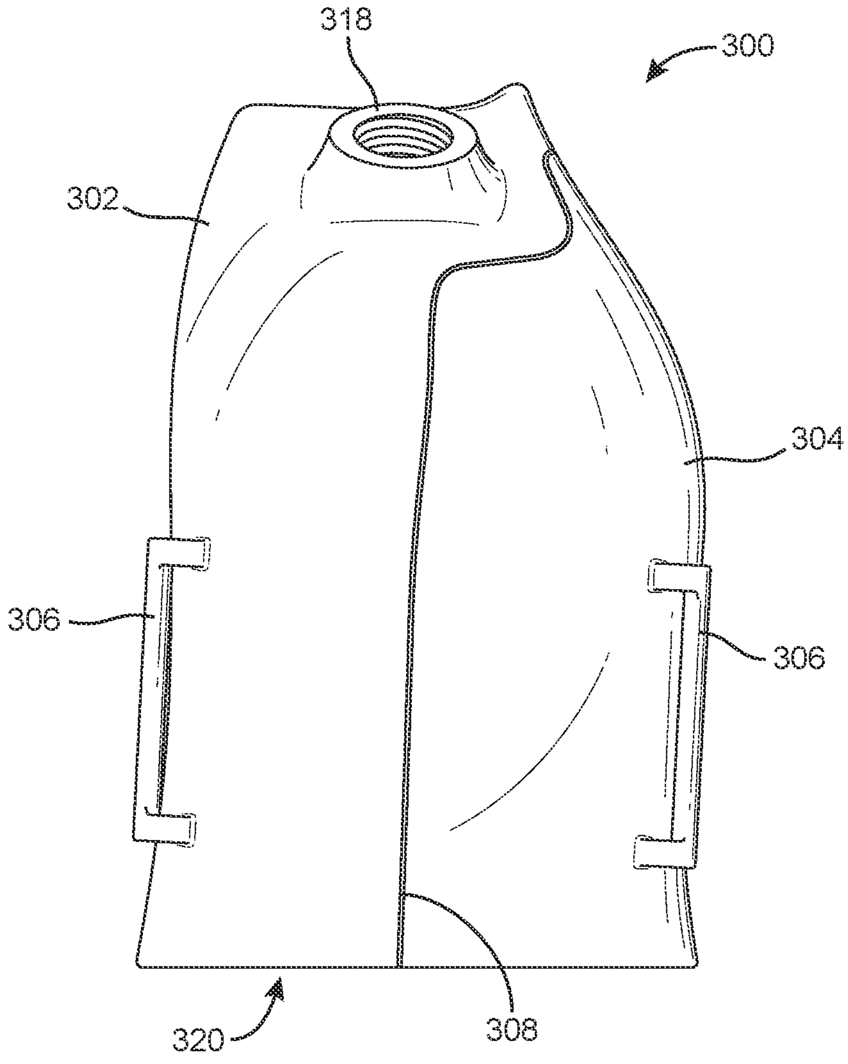
FIG. 1 is a front view of a residual limb protective device, according to some embodiments.

Before turning to the FIGURES, which illustrate the exemplary embodiments in detail, it should be understood that the present application is not limited to the details or methodology set forth in the description or illustrated in the FIGURES. It should also be understood that the terminology is for the purpose of description only and should not be regarded as limiting.

Overview

Referring generally to the FIGURES, additive manufacturing is used to produce prosthetic, orthotic, and/or protective devices with variable wall thickness. The variable wall thickness facilitates improved fit and comfort, and can facilitate distribution of stresses.

The prosthetic, orthotic, and/or protective device may have variable cross-sectional thickness. The thickness of the protective device can vary throughout based on the anatomy of the patient's residual limb as well as the requirements of the patient for use and functionality. The variable thickness can provide flexibility in areas of increased motion as well as provide increased structural support to areas of high stress.

The protective device may be an upper extremity post-operative residual limb protector that is designed to fit a partial hand of a patient wearing the device, according to some embodiments. In some embodiments, the upper extremity post-operative residual limb protector utilizes a 3D scan of the patient's residual limb or a 3D scan of a cast of the patient's residual limb during the design process. This is done to ensure that the device fits the contours and exact anatomy of the patient's hand, according to some embodiments.

In some embodiments, the upper extremity post-operative residual limb protector utilizes a hinge system for opening and closing the device. At least one strap is applied to the outer shell to fasten the device in place around the patient's hand, according to some embodiments. The strap and hinge systems provide the patient with an easy-on and easy-off application of the device, according to some embodiments.

In some embodiments, the upper extremity post-operative residual limb protector can have extra attachments included in the design of the device to provide additional functionality to the patient's partial hand. In some embodiments, the upper extremity post-operative residual limb protector has the majority of its components produced via additive manufacturing with the use of a 3D scan file. A 3D scan of the patient's residual limb or a 3D scan of a cast of the patient's residual limb is used during the design process to ensure that the device fits the contours and exact anatomy of the patient's hand, according to some embodiments. The creation of a positive offset model as well as the application of build-ups and modifications are done to the base scan to create the design of the device, according to some embodiments.

In some embodiments, the upper extremity post-operative residual limb protector is produced via additive manufacturing. The shell, hinge system, strap mounting hardware, and any additional attachments are constructed layer by layer using a 3D printer, according to some embodiments. With the exception of straps that are attached in post-processing, the entire device may be constructed using a uniform material composition, according to some embodiments. The techniques described herein for additive manufacturing can additionally be used to manufacture the prosthetic, orthotic, connection insert, or related medical devices as described in U.S. Patent Application Pub. No. 2018/0353308 A1, filed Jul. 31, 2018, the entire disclosure of which is incorporated by reference herein. Further, any of the additive manufacturing techniques as described in U.S. Patent Application Pub. No. 2018/0353308 A1 may be used to manufacture any of the devices described herein.

In some embodiments, the prosthetic, orthotic, connection insert, protective device, etc., as described herein are manufactured using any of the techniques as described in U.S. Pat. No. 10,766,246 B2, filed Dec. 15, 2014, the entire disclosure of which is incorporated by reference herein.

Protective Device

Figure 2:
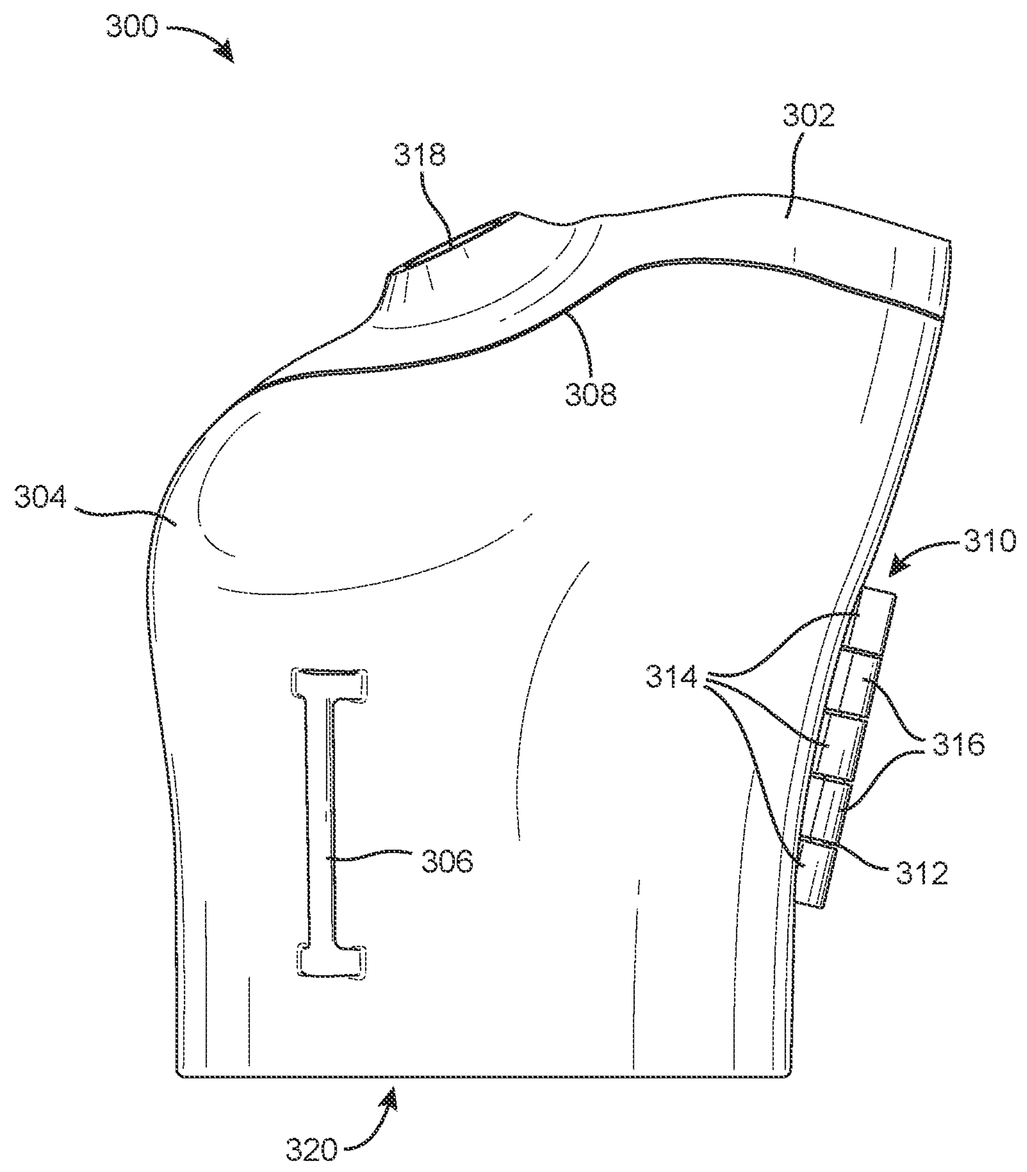
FIG. 2 is a side view of the residual limb protective device of FIG. 1, according to some embodiments.
Figure 3:
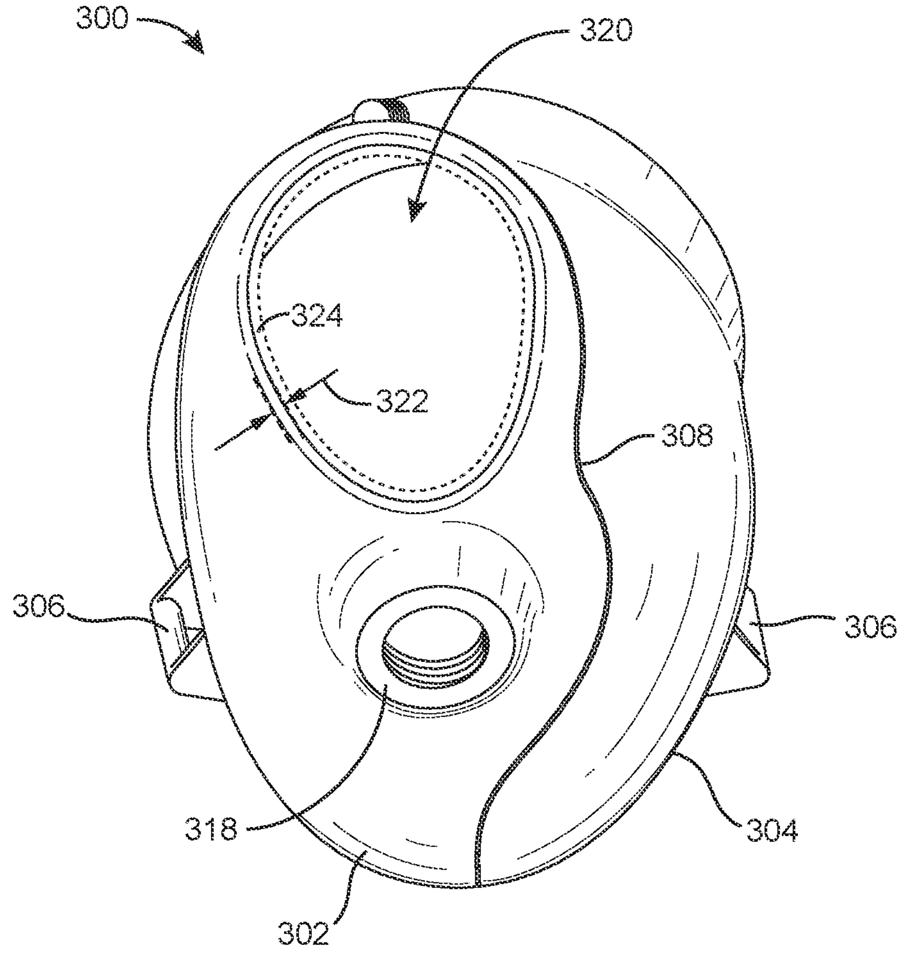
FIG. 3 is a top view of the residual limb protective device of FIG. 1, according to some embodiments.

Referring now to FIGS. 1-3, a protective device, a protector, etc., shown as protective device 300 is shown, according to some embodiments. Protective device 300 can be for an upper extremity post-operative residual limb of a patient. Protective device 300 can be configured to fit contours of the patient's residual limb and may enclose around a patient's partial hand or residual limb.

Protective device 300 can be a multi-sectional device including a first section, a first portion, a first part, etc., shown as first shell 302 and a second section, a second portion, a second part, etc., shown as second shell 304. First shell 302 and second shell 304 are configured to hingedly, pivotally, or rotatably couple with each other through a hinge system, shown as hinge 310. Hinge 310 is configured to facilitate relative rotation between first shell 302 and second shell 304 so that the protective device can be transitioned between an open position or configuration (e.g., a first state) and a closed position or configuration (e.g., a second state).

Hinge 310 includes a pin 312, first members 314, and second members 316. First members 314 can be knuckles configured to receive the pin 312 therethrough and fixedly couple with first shell 302 or second shell 304. Second members 316 can similarly be knuckles configured to receive the pin 312 therethrough and fixedly couple with the other one of first shell 302 or second shell 304.

First shell 302 and second shell 304 are configured to cooperatively define an inner volume 320 (e.g., an inner cavity, a void etc.), according to some embodiments. In some embodiments, first shell 302 and second shell 304 are configured to interlock with each other along cut line 308. For example, an edge of first shell 302 and a corresponding edge of second shell 304 can correspond to each other so that first shell 302 and second shell 304 interlock with each other.

Referring particularly to FIG. 1, protective device 300 includes strap hardware 306, according to some embodiments. For example, first shell 302 can have strap hardware 306 that is integrally formed or fixedly coupled with first shell 302. Similarly, second shell 304 can have strap hardware 306 that is integrally formed or fixedly coupled with second shell 304. Strap hardware 306 can be configured to receive a strap. The strap may fasten with itself to secure protective device into the closed position.

Referring to FIGS. 1-3, protective device 300 (or more particularly first shell 302) includes an accessory engagement portion 318. Accessory engagement portion 318 can be a bore that extends through first shell 302 and includes threads for attachment or coupling of one or more accessories (e.g., hooks, a grabbing mechanism, an offset post, etc.) to protective device 300. The threads may be printed onto the protective device 300 and can facilitate improved functionality when paired with threaded device attachments.

In some embodiments, protective device 300 can be augmented to allow for continued usability of the patient's residual limb with little to no interference from a shape or weight of the protective device 300 when in use. Protective device 300 can also provide protection to a post-operative site at the residual limb.

Referring particularly to FIG. 3, first shell 302 and second shell 304 each have a thickness 322. Thickness 322 may be non-uniform across first shell 302 and/or second shell 304. The thickness 322 at different locations, positions, areas, or regions can be based on anatomy or requirements of the patient for protective and/or functional purposes. The first shell 302 and the second shell 304 can include variable thickness 322 to achieve desired flexion in different regions or areas. In some embodiments, a thickness of first shell 302 and second shell 304 across the entirety of first shell 302 and the second shell 304 is based on (e.g., set, adjusted, etc.) or corresponds to anatomy or requirements of the patient for protective or functional purposes.

The protective device 300 may also include an optional foam or gauze layer, shown as inner lining 324, according to some embodiments. In some embodiments, the inner lining 324 is a foam layer that extends along an entirety of an interior surface of the first shell 302 and the second shell 304. In some embodiments, a protective layer or gauze layer can be placed over the patient's residual limb for scanning and/or fitting of the protective device 300. In some embodiments, the inner lining 324 is optional.

In some embodiments, the first and second shells 302-304, the hinge 310, the strap mounting hardware 306, and any additional accessories are manufactured from a same material (e.g., a thermoplastic such as nylon). In some embodiments, heat can be applied to the first and second shells 302-304, the strap mounting hardware 306, or the additional accessories so that minor adjustments or plastic deformations can be made. In some embodiments, the first and second shells 302-304, the strap mounting hardware 306, and the hinge 310 can be manufactured or produced via additive manufacturing. In some embodiments, the first and second shells 302-304, the strap mounting hardware 306, and the hinge 310 are manufactured using 3d printing, by dispensing material (e.g., one or more materials that can form nylon when combined with fusing/detailing agents and exposed to fusing light, or any other dispensable material) in subsequent layers. The one or more materials may be dispensed or output in a powder form. The one or more materials (e.g., in the powder form) that form nylon when combined with fusing/detailing agents and exposed to fusing lighting can be used in the manufacturing of the protective device 300.

The first shell 302 and the second shell 304 have variable thickness 322 that may transition between different spatial locations along the first shell 302 and/or the second shell 304. The thickness 322 of the first shell 302 and/or the second shell 304 may be uniform or may vary spatially at different positions. For example, areas of the first shell 302 and/or the second shell 304 that are anticipated or expected to undergo higher stress may have an increased thickness relative to other areas that are expected to undergo lower stress during use of the protective device 300 (or vice versa). In some embodiments, different areas of the first shell 302 and/or the second shell 304 that should deform to a shape of the user's residual limb have a decreased thickness to facilitate controlled flexing or bending of the first shell 302 and/or the second shell 304 to facilitate comfort and proper fit of the protective device 300. In some embodiments, the thickness of the shell 301 increases from one end to another end of the first shell 302 and/or the second shell 304 so that the thickness 322 of the first shell 302 and/or the second shell 304 proximate the one end is greater than thickness of the shell 301 at the other end. In some embodiments, variation of the thickness of the shell 301 is configured based on patient activity level, weight, etc.

Figure 4:
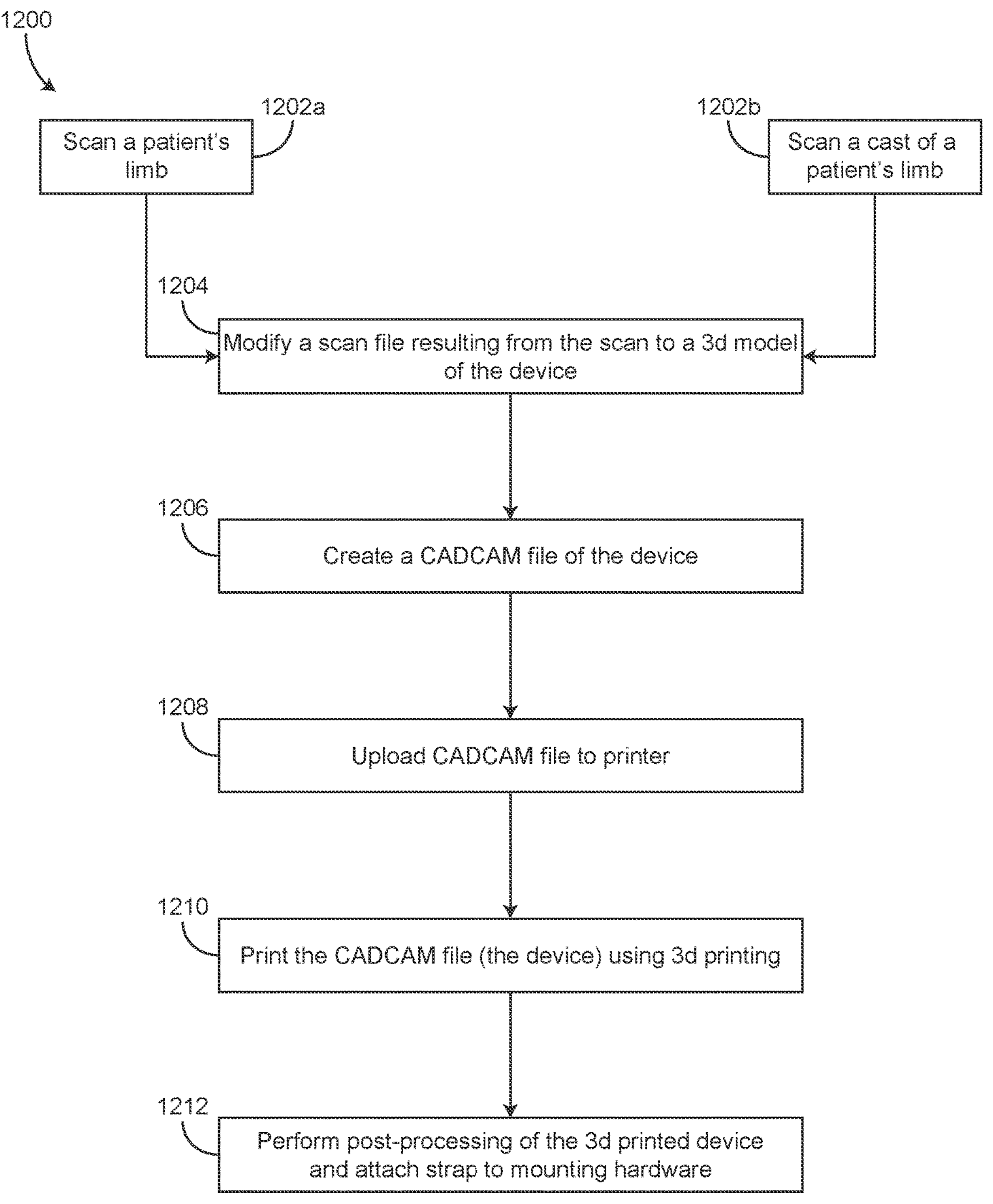
FIG. 4 is a flow diagram of a process for manufacturing the residual limb protective device of FIGS. 1-3, according to some embodiments.

Referring particularly to FIG. 4, a flow diagram of a process 1200 for producing or manufacturing the protective device 300 of FIGS. 1-3 is shown, according to some embodiments. Process 1200 includes steps 1202-1212 and can be performed using an additive manufacturing system (e.g., system 1300 as described in greater detail below with reference to FIG. 5).

Process 1200 includes scanning a patient's limb (step 1202*a*) or scanning a cast of a patient's limb (step 1202*b*). In some embodiments, step 1202*a* or step 1202*b* is performed using a scanning device (e.g., scan device 1312 as described in greater detail below with reference to FIG. 5). The patient's limb can be scanned directly (step 1202*a*), or a cast of the patient's limb may be scanned (step 1202*b*). In some embodiments, performing step 1202*a* or step 1202*b* results in the generation of a scan file. In some embodiments, a protective gauze or dressing is placed over the patient's limb prior to scanning and/or fitting.

Process 1200 includes modifying a scan file resulting from the scan (e.g., resulting from performing step 1202*a* or step 1202*b*) to a 3d model of a device (e.g., the protective device 300) (step 1204), according to some embodiments. In some embodiments, step 1204 is performed on a computer system based on one or more user inputs or inputs from a health care provider. For example, step 1204 can include adjusting a thickness of the device of the scan file at different locations. In some embodiments, step 1204 includes digitally using buildups or reductions to the thickness of the 3d model of the device to achieve a desired thickness that yields a desired corresponding deformation or flexion when the device is loaded. For example, step 1204 can be performed by computer system 1302 based on one or more user inputs or inputs from a health care provider obtained from user device 1310 (described in greater detail below with reference to FIG. 5).

Process 1200 includes creating a computer assisted design (CAD) and/or a computer assisted manufacturing (CAM) file of the device (e.g., the protective device 300) (step 1206), according to some embodiments. Process 1200 also includes uploading the CAD/CAM file to a printer (e.g., 3d printer 1314) (step 1208), according to some embodiments. Steps 1206 and 1208 can be performed by computer system 1302 (e.g., in response to a user input such as from a health care provider) as described in greater detail below with reference to FIG. 5.

Process 1200 includes printing the CAD/CAM file using 3d printing (e.g., to generate the device, the prosthetic socket 100, etc.) (step 1210), according to some embodiments. In some embodiments, step 1210 includes performing additive manufacturing (e.g., dispensing or outputting layers consecutively on top of each other) to produce the device. In some embodiments, the additive manufacturing is performed using a single uniform material such as a thermoplastic (e.g., nylon). The resulting device or 3d printed component can have variable thickness as defined by the CAD/CAM file.

Process 1200 includes performing post-processing on the 3d printed device and attaching a strap to mounting hardware (step 1212), according to some embodiments. For example, step 1212 can include removing excess material that is dispensed during step 1210 (e.g., during fabrication of the device). Step 1212 can be performed by a technician. Additional post-processing can be performed based on anatomy or needs of the patient. In some embodiments, the strap is configured to fasten with itself to secure the 3d printed device in a closed configuration.

In some embodiments, the device that is produced by performing process 1200 is a protective device, with a varying thickness (e.g., cross-sectional thickness) throughout. The device can provides proper stability and distribution of forces when worn, and is produced using additive manufacturing techniques. The thickness of the device can be modified in any area to accommodate the anatomy of the patient as well as any additional requirements the patient may have. The device is created using 3D printing, wherein the material composition is of a single uniform substance and can provide extra comfort to the patient when worn due to its lightweight properties, according to some embodiments.

Additive Manufacturing System Architecture

Figure 5:
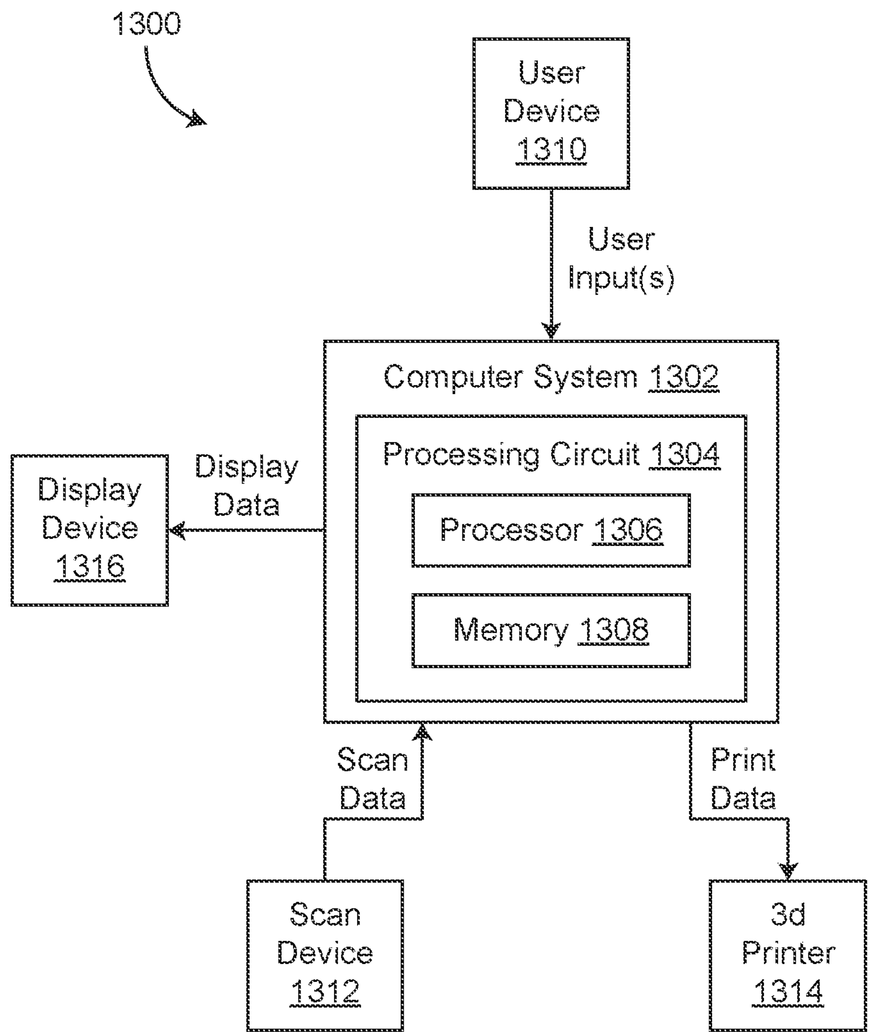
FIG. 5 is a system for additive manufacturing that can be used to manufacture the residual limb protective device of FIGS. 1-3, according to some embodiments.

Referring now to FIG. 5, a system 1300 for additive manufacturing of prosthetic, orthotic, or protective devices is shown, according to some embodiments. System 1300 includes a user device 1310, a display device 1316, a computer system 1302, a scan device 1312, and a 3d printer or additive manufacturing machine 1314.

Computer system 1302 is configured to receive scan data from scan device 1312, according to some embodiments. Computer system 1302 can be a desktop computer, a laptop, a remote computing system, a smart phone, a tablet, a personal computing device, etc. Computer system 1302 includes a processing circuit 1304 having memory 1308 and a processor 1306. Processor 1306 can be implemented as a general-purpose processor, an application specific integrated circuit (ASIC), one or more field programmable gate arrays (FPGAs), a group of processing components, or other suitable electronic processing components.

Memory 1308 (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present application. Memory 1308 may be or include volatile memory or non-volatile memory. Memory 1308 may include database components, object code components, script components, or any other type of information structure for supporting the various activities and information structures described in the present application. According to an exemplary embodiment, memory 1308 is communicably connected to processor 1306 via processing circuit 1304 and includes computer code for executing (e.g., by processing circuit 1304 and/or processor 1306) one or more processes described herein.

Computer system 1302 can be configured to run CAD computer software to facilitate the design and production of any of prosthetic socket, orthotic device, and/or protective device 300. Computer system 1302 is configured to receive scan data from scan device 1312, according to some embodiments. In some embodiments, the scan data is a scan file obtained from scan device 1312. In some embodiments, a technician may scan device 1312 to scan a patient's residual limb or a cast of the patient's residual limb, thereby generating the scan data.

When the scan data is provided to computer system 1302, computer system 1302 can generate a CAD or CAM file. A user (e.g., a health care provider) can then provide inputs (e.g., via user device 1310) to adjust geometry, thickness, etc., of the CAD or CAM file. More generally, computer system 1302 may use the scan data to generate a digital representation of a device to be manufactured for the patient's residual limb. Computer system 1302 can provide display data to display device 1316 (e.g., a computer screen, a display screen, etc.) so that the digital representation is visually displayed in real-time. The user or health care provider can then view real-time changes or updates as the user changes or adjusts the CAD or CAM file.

For example, the user may adjust the CAD or the CAM file so that the design gradually tapers or thickens in different areas. In some embodiments, the user or the health care provider may use data from different experiments to identify areas where a patient may experience high stress. The user may decrease thickness of the CAD or CAM file at areas where high stress is experienced so that the 3d printed device may flex or deform. This can allow the 3d printed device to be more comfortable for the patient. In some embodiments, thickness of the 3d printed devices is maintained above a minimum thickness value. The user can also use knowledge regarding different weight lines of the patient to determine which areas of the CAD or CAM file/model should have decreased or increased thickness. The user may also use historical data to determine which areas or portions of the 3d printed device or the CAD/CAM file/model should have increased or decreased thickness (e.g., wall thickness).

Once the user (e.g., the health care provider) has adjusted or manipulated the CAD/CAM file/model, the user can prompt computer system 1302 to export the file/model to 3d printer 1314 as print data. Computer system 1302 can convert the adjusted, manipulated, or updated CAD/CAM file/model to a file type that is compatible with 3d printer 1314 (e.g., a Standard Tessellation Language (STL) file). Computer system 1302 then provides the print data to 3d printer 1314.

The 3d printer 1314 can be any additive manufacturing machine or device that is configured to successively provide or discharge layers of material onto each other to form or construct a part. 3d printer 1314 may be configured to dispense material (e.g., one or more powder materials that can form nylon when combined with fusing/detailing agents and exposed to fusing light, or any other dispensable materials) in layers to fabricate the CAD/CAM file.

Advantageously, the systems and methods described herein can be used to produce 3d printed prosthetics, orthotics, or protective devices. Traditional molding methods do not offer the same flexibility of variable wall thickness as does additive manufacturing. The variable wall thickness is achieved using additive manufacturing (e.g., 3d printing) and can facilitate improved fit, comfort, and stress distribution.

Configuration of Exemplary Embodiments

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claim.

It should be noted that the terms "exemplary" and "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent, etc.) or moveable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," "between," etc.) are merely used to describe the orientation of various elements in the figures. It should be noted that the orientation of various elements may differ according to other exemplary embodiments, and that such variations are intended to be encompassed by the present disclosure.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

It is important to note that the construction and arrangement of the systems as shown in the exemplary embodiments is illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claim.

What is claimed is:

1. A protective device for an upper extremity post-operative residual limb of a user, the protective device comprising:

a multi-section shell comprising a shape that corresponds to an anatomical structure of the upper extremity post-operative residual limb of the user;

a hinge coupled with a first section and a second section of the multi-section shell, the hinge configured to facilitate relative rotation of the first section and the second section to transition the protective device between an open configuration and a closed configuration;

wherein the first section of the multi-section shell includes an attachment engagement portion, wherein threads of the attachment engagement portion are configured to receive one or more attachments to increase functionality of the upper extremity post-operative residual limb of the user, wherein the multi-sectional shell comprises a wall thickness that varies spatially along the multi-section shell, the wall thickness at a particular location being based on a corresponding amount of expected stress to be experienced by the multi-section shell at the particular location during use of the protective device, wherein the variable thickness enables a desired corresponding flexion at the particular location, the multi-section shell having a shape modified from a scan shape associated with a scan of the upper extremity post-operative residual, wherein the multi-sectional shell comprises a foam layer extending longitudinally along an entirety of an interior of the multi-section shell and configured to directly abut the upper extremity post-operative residual limb of the user.

2. The protective device of claim 1, wherein the protective device is configured for use with a patient's partial hand.

3. The protective device of claim 2, wherein the multi-section shell is configured to fully enclose around the patient's partial hand.

4. The protective device of claim 1, wherein the one or more attachments are implemented in a design process of the protective device to supplement the user's ability to interact with surroundings.

5. The protective device of claim 1, wherein the multi-section shell is configured to undergo deformation without sustaining structural damage, and wherein the multi-sectional shell is made by additive manufacturing and the modified shape is achieved by modifying the scan data, thereby providing a wall surface that has not been modified by mechanical cutting.

6. The protective device of claim 1, further comprising:

one or more fitted straps configured to couple with strap mounting portions, the straps configured to fasten with themselves.

7. The protective device of claim 1, wherein the multi-section shell is configured to fit contours and structures of the upper extremity post-operative residual limb of the user, wherein the multi-section shell comprises a foam layer positioned on an interior of the multi-section shell and configured to directly abut the upper extremity post-operative residual limb of the user.

8. A protective device for an upper extremity post-operative residual limb of a user manufactured using additive manufacturing, the protective device comprising:

a multi-section shell comprising a shape that corresponds to an anatomical structure of the upper extremity post-operative residual limb of the user;

a hinge coupled with a first section and a second section of the multi-section shell, the hinge configured to facilitate relative rotation of the first section and the second section to transition the protective device between an open configuration and a closed configuration;

a single attachment engagement portion configured to receive one or more attachments to increase functionality of the upper extremity post-operative residual limb of the user;

wherein the multi-section shell has a wall thickness that varies spatially along the multi-section shell, the wall thickness at a particular location being based on a corresponding amount of expected stress to be experienced by the multi-section shell at the particular location during use of the protective device, wherein the variable thickness enables a desired corresponding flexion at the particular location, the multi-section shell having a shape modified from a scan shape associated with a scan of the upper extremity post-operative residual, wherein the multi-sectional shell comprises a foam layer extending along an entirety of an interior of the multi-section shell and configured to directly abut the upper extremity post-operative residual limb of the user.

9. The protective device of claim 8, wherein the multi-section shell is configured to receive one or more attachments to increase functionality of the upper extremity post-operative residual limb of the user.

10. The protective device of claim 8, wherein the protective device is configured for use with a patient's partial hand.

11. The protective device of claim 10, wherein the multi-section shell is configured to fully enclose around the patient's partial hand.

12. The protective device of claim 8, wherein the multi-section shell is configured to undergo deformation without sustaining structural damage.

13. The protective device of claim 8, further comprising:

one or more fitted straps configured to couple with strap mounting portions, the straps configured to fasten with themselves.

14. The protective device of claim 8, wherein the multi-section shell is configured to fit contours and structures of the upper extremity post-operative residual limb of the user, wherein the multi-section shell comprises a foam layer positioned on an interior of the multi-section shell and configured to directly abut the upper extremity post-operative residual limb of the user.

15. The protective device of claim 5, wherein the multi-section shell and the hinge comprise a plurality of layers of material integrally formed with each other.

16. The protective device of claim 8, wherein the multi-section shell and the hinge comprise a plurality of layers of material integrally formed with each other.

17. A protective device for an upper extremity post-operative residual limb of a user manufactured using additive manufacturing, the protective device comprising:

a multi-section shell comprising a shape that corresponds to an anatomical structure of the upper extremity post-operative residual limb of the user;

a hinge coupled with a first section and a second section of the multi-section shell, the hinge configured to facilitate relative rotation of the first section and the second section to transition the protective device between an open configuration and a closed configuration;

a single attachment engagement portion configured to receive one or more attachments to increase functionality of the upper extremity post-operative residual limb of the user;

wherein the multi-section shell has a wall thickness that varies spatially along the multi-section shell, wherein the wall thickness at a particular location being based on a corresponding amount of expected stress to be experienced by the multi-section shell at the particular location during use of the protective device, wherein the variable thickness enables a desired corresponding flexion at the particular location, the multi-section shell having a shape modified from a scan shape associated with a scan of the upper extremity post-operative residual, wherein the multi-sectional shell comprises a foam layer extending along an entirety of an interior of the multi-section shell and configured to directly abut the upper extremity post-operative residual limb of the user.

18. The protective device of claim 17, wherein the thickness at a particular location is determined based on a corresponding amount of expected stress to be experienced by the multi-section shell at the particular location during use of the protective device while worn by the user.

19. The protective device of claim 17, wherein the multi-section shell is configured to fit contours and structures of the upper extremity post-operative residual limb of the user, wherein the multi-section shell comprises a foam layer positioned on an interior of the multi-section shell and configured to directly abut the upper extremity post-operative residual limb of the user.

20. The protective device of claim 17, wherein the multi-sectional shell is made by additive manufacturing and the modified shape is achieved by modifying the scan data, thereby providing a wall surface that has not been modified by mechanical cutting.

* * * * *